(12) United States Patent
Abhari et al.

(10) Patent No.: US 11,672,609 B2
(45) Date of Patent: *Jun. 13, 2023

(54) METHODS AND SYSTEMS FOR PROVIDING DEPTH INFORMATION

(71) Applicant: Synaptive Medical Inc., Toronto (CA)

(72) Inventors: Kamyar Abhari, Toronto (CA); Gal Sela, Toronto (CA); Michael Frank Gunter Wood, Toronto (CA); Kai Michael Hynna, Toronto (CA); Kelly Noel Dyer, Toronto (CA); Tammy Kee-wai Lee, Toronto (CA)

(73) Assignee: Synaptive Medical Inc.

( * ) Notice: Subject to any disclaimer, the term of this patent is extended or adjusted under 35 U.S.C. 154(b) by 164 days.

This patent is subject to a terminal disclaimer.

(21) Appl. No.: 17/094,777

(22) Filed: Nov. 10, 2020

(65) Prior Publication Data
US 2021/0228283 A1    Jul. 29, 2021

Related U.S. Application Data

(63) Continuation of application No. 16/343,248, filed as application No. PCT/CA2016/051223 on Oct. 21, 2016, now Pat. No. 10,828,114.

(51) Int. Cl.
*A61B 34/20* (2016.01)
*G06T 7/50* (2017.01)
(Continued)

(52) U.S. Cl.
CPC .............. *A61B 34/20* (2016.02); *G06T 5/002* (2013.01); *G06T 7/20* (2013.01); *G06T 7/50* (2017.01);
(Continued)

(58) Field of Classification Search
CPC ............ A61B 34/20; A61B 2034/2057; A61B 2017/00128; A61B 2034/107; A61B 2034/2055; A61B 2034/2068; A61B 90/37; A61B 34/76; A61B 2090/061; A61B 2090/062; A61B 2090/363;
(Continued)

(56) References Cited

U.S. PATENT DOCUMENTS

2004/0106916 A1* 6/2004 Quaid .................... A61B 34/71
606/1
2009/0116732 A1    5/2009 Zhou
(Continued)

FOREIGN PATENT DOCUMENTS

| WO | 2005009215 A2 | 2/2005 |
| WO | 2016065457 A1 | 5/2016 |
| WO | 2016108110 A1 | 7/2016 |

*Primary Examiner* — Jianxun Yang

(57) ABSTRACT

Methods and systems for outputting depth data during a medical procedure on a patient. Depth data is outputted, representing at least one of relative depth data and general depth data. Tracking information about the position and orientation of a medical instrument and depth information about variations in depth over a site of interest are used. Relative depth data represents the depth information relative to the position and orientation of the instrument. General depth data represents the depth information over the site of interest independently of the position and orientation of the instrument.

17 Claims, 16 Drawing Sheets

(51) Int. Cl.
*G06T 7/70* (2017.01)
*G06T 5/00* (2006.01)
*G06T 7/20* (2017.01)

(52) U.S. Cl.
CPC ........ *G06T 7/70* (2017.01); *A61B 2034/2057* (2016.02)

(58) Field of Classification Search
CPC ...... A61B 2090/373; A61B 2090/3735; G06T 5/002; G06T 7/20; G06T 7/50; G06T 7/70
See application file for complete search history.

(56) References Cited

U.S. PATENT DOCUMENTS

| | | | |
|---|---|---|---|
| 2014/0221822 A1* | 8/2014 | Ehlers | A61B 5/061 600/424 |
| 2014/0267603 A1 | 9/2014 | Kerdok | |
| 2016/0117857 A1* | 4/2016 | State | G06T 19/00 345/420 |
| 2016/0249987 A1 | 9/2016 | Hladio | |
| 2018/0325601 A1* | 11/2018 | Mak | A61B 5/0066 |

* cited by examiner

METHODS AND SYSTEMS FOR PROVIDING DEPTH INFORMATION

CROSS-REFERENCE TO RELATED APPLICATION

This application is a continuation of U.S. patent application Ser. No. 16/343,248 filed Apr. 18, 2019, titled METHODS AND SYSTEMS FOR PROVIDING DEPTH INFORMATION, the contents of which are hereby expressly incorporated into the present application by reference in its entirety.

FIELD

The present disclosure is generally related to methods and systems providing depth information, including providing depth information about a surgical site relative to a medical instrument. Such methods and systems may be used during image guided medical procedures.

BACKGROUND

The present disclosure may be useful for image guided medical procedures using a surgical instrument. Image guidance may be provided by, for example, an optical scope, an optical coherence tomography (OCT) probe, or a micro ultrasound transducer. The medical procedure may be an access port-based surgery.

In an example port-based surgery, a surgeon or a robotic surgical system may perform a surgical procedure involving tumor resection in the brain. A goal of the procedure typically includes minimizing the trauma to healthy tissue, such as the intact white and grey matter of the brain. Trauma may occur, for example, due to contact of healthy tissue with the access port, stress to the brain matter, unintentional impact with surgical devices, and/or accidental resection of healthy tissue. In order to reduce trauma, the surgeon should have accurate information, including depth information, about where the surgical tools are relative to the surgical site of interest.

In another example, during endoscopic third ventriculostomy (ETV), the surgeon may find it difficult to locate the basilar artery beneath the third ventricle if the tissue is thick and opaque. In those cases, depth information may be useful to identify the location of the artery and thus avoid injuring it.

Conventional systems may not provide information about the surgical site in sufficient detail. For example, when a port-based surgery is being performed, the surgeon's view down the access port is often restricted and the surgeon typically relies on a view of the surgical site of interest provided by a scope and shown on a display in the operating room. Conventionally, this view is a two dimensional (2D) image, which have limitations for providing information about the three-dimensional (3D) surgical site.

It would be desirable to have a system that provides a surgeon with information about the 3D aspects of the surgical site. 3D depth information is beneficial for surgeons to use during medical procedures as it is expected to improve tool manipulation within the area of interest on a tissue of interest when viewing the field. However, it may be difficult to provide such information in cases where a 3D display (also known as a stereo display) is not used.

SUMMARY

In some examples, the present disclosure describes a medical navigation system for use during a medical procedure on a patient. The medical navigation system includes a tracking system, a depth detector and a controller. The tracking system is configured to obtain tracking information about position and orientation of an instrument during the medical procedure. The depth detector is configured to obtain depth information about variations in depth over a site of interest. The controller is in communication with the tracking camera and the depth detector to receive the tracking information and the depth information, respectively. The controller has a processor coupled to a memory, and the controller is configured to cause at least one output device to provide output representing at least one of relative depth data and general depth data. The relative depth data is determined by the controller using the tracking information and the depth information, and represents the depth information relative to the position and orientation of the instrument. The general depth data represents the depth information over the site of interest independently of the position and orientation of the instrument.

In some examples, the present disclosure describes a method for use during a medical procedure on a patient. Depth information is received about variations in depth over a site of interest. Tracking information is received about position and orientation of an instrument during the medical procedure. Output is provided representing at least one of relative depth data and general depth data. The relative depth data is determined using the tracking information and the depth information, and represents the depth information relative to the position and orientation of the instrument. The general depth data represents the depth information over the site of interest independently of the position and orientation of the instrument.

BRIEF DESCRIPTION OF THE DRAWINGS

Reference will now be made, by way of example, to the accompanying drawings which show example embodiments of the present application, and in which.

Embodiments will now be described, by way of example only, with reference to the drawings, in which.

Similar reference numerals may have been used in different figures to denote similar components.

DESCRIPTION OF EXAMPLE EMBODIMENTS

Figure 1:
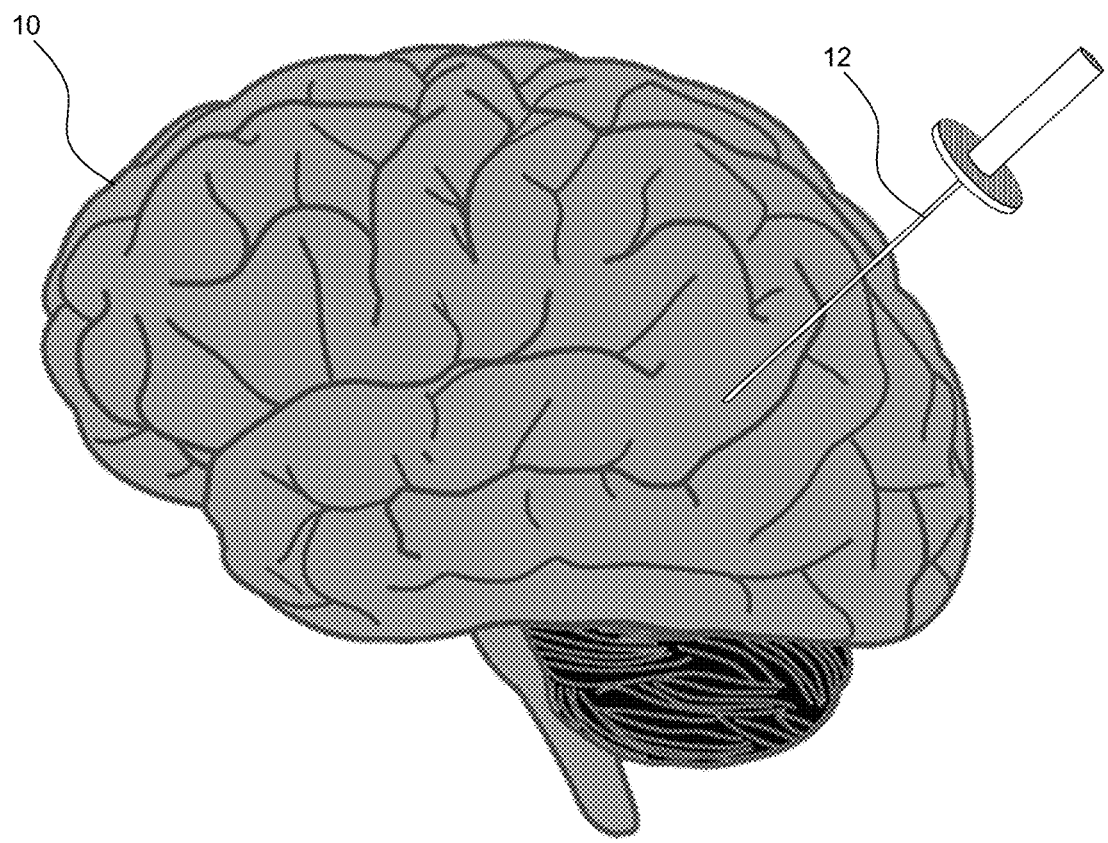
FIG. 1 illustrates the insertion of an access port into a human brain, for providing access to internal brain tissue during an example medical procedure.

The systems and methods described herein may be useful in the field of neurosurgery, including oncological care, neurodegenerative disease, stroke, brain trauma and orthopedic surgery. The teachings of the present disclosure may be applicable to other conditions or fields of medicine. It should be noted that while the present disclosure describes examples in the context of neurosurgery, the present disclosure may be applicable to other procedures that may benefit from providing depth information to the surgeon or other operator.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" or "example" means "serving as an example, instance, or illustration," and should not be construed as preferred or advantageous over other configurations disclosed herein.

As used herein, the terms "about", "approximately", and "substantially" are meant to cover variations that may exist in the upper and lower limits of the ranges of values, such as variations in properties, parameters, and dimensions. In one non-limiting example, the terms "about", "approximately", and "substantially" mean plus or minus 10 percent or less.

Unless defined otherwise, all technical and scientific terms used herein are intended to have the same meaning as commonly understood by one of ordinary skill in the art. Unless otherwise indicated, such as through context, as used herein, the following terms are intended to have the following meanings:

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Some embodiments of the present disclosure provide imaging devices that are insertable into a subject or patient for imaging internal tissues, and methods of use thereof. Some embodiments of the present disclosure relate to minimally invasive medical procedures that are performed via an access port, whereby surgery, diagnostic imaging, therapy, or other medical procedures (e.g., minimally invasive medical procedures) are performed based on access to internal tissue through the access port.

FIG. 1 illustrates the insertion of an access port into a human brain, for providing access to internal brain tissue during a medical procedure. In FIG. 1, an access port 12 is inserted into a human brain 10, providing access to internal brain tissue. The access port 12 may include such instruments as catheters, surgical probes, or cylindrical ports such as the NICO BrainPath™. Surgical tools and instruments may then be inserted within the lumen of the access port in order to perform surgical, diagnostic or therapeutic procedures, such as resecting tumors as necessary.

The present disclosure applies equally well to catheters, deep brain stimulation (DBS) needles, a biopsy procedure, and also to biopsies and/or catheters in other medical procedures performed on other parts of the body, as well as to medical procedures that do not use an access port.

In the example of a port-based surgery, a straight or linear access port 12 is typically guided down a sulcal path of the brain. Surgical instruments would then be inserted down the access port 12. Optical tracking systems, used in the medical procedure, track the position of a part of the instrument that is within line-of-sight of the optical tracking camera. Other tracking systems may be used, such as electromagnetic, optical, or mechanical based tracking systems.

Figure 2:
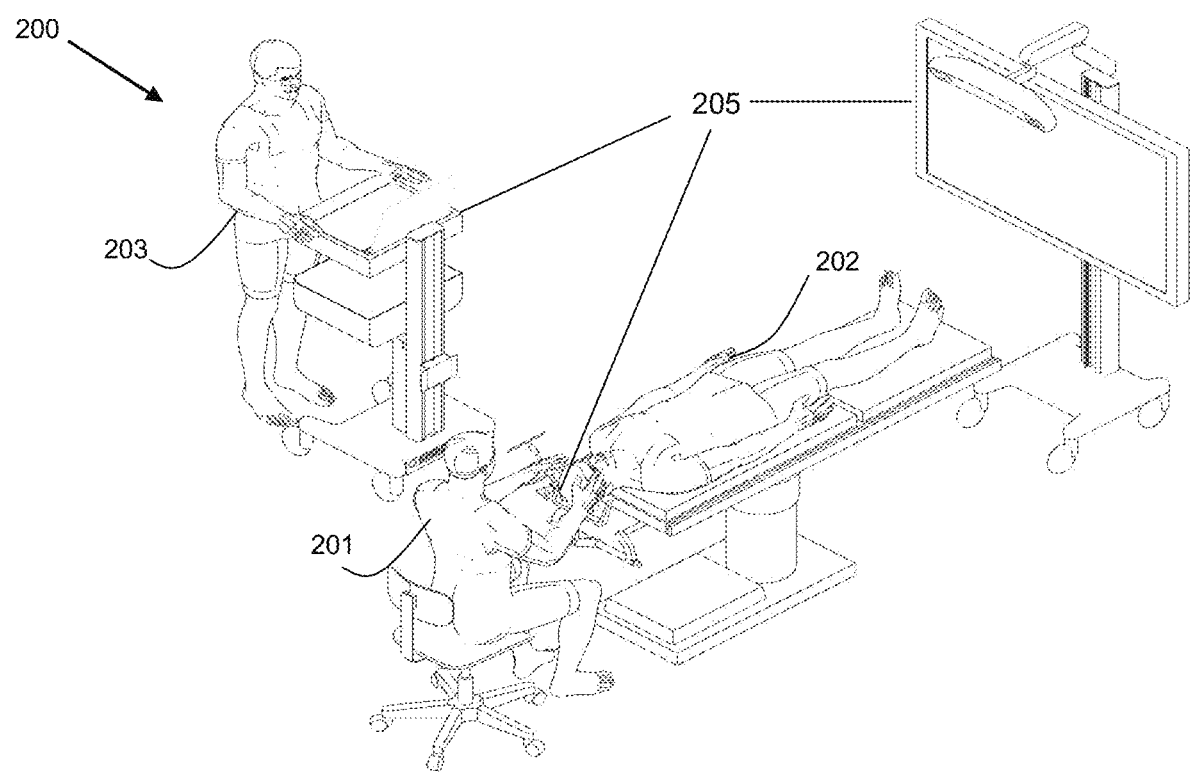
FIG. 2 shows an example navigation system to support image guided surgery.

In FIG. 2, an exemplary navigation system environment 200 is shown, which may be used to support navigated image-guided surgery. As shown in FIG. 2, a surgeon 201 conducts a surgery on a patient 202 in an operating room (OR) environment. A medical navigation system 205 may include an equipment tower, tracking system, displays and tracked instruments to assist the surgeon 201 during the procedure. An operator 203 may also be present to operate, control and provide assistance for the medical navigation system 205.

Figure 3:
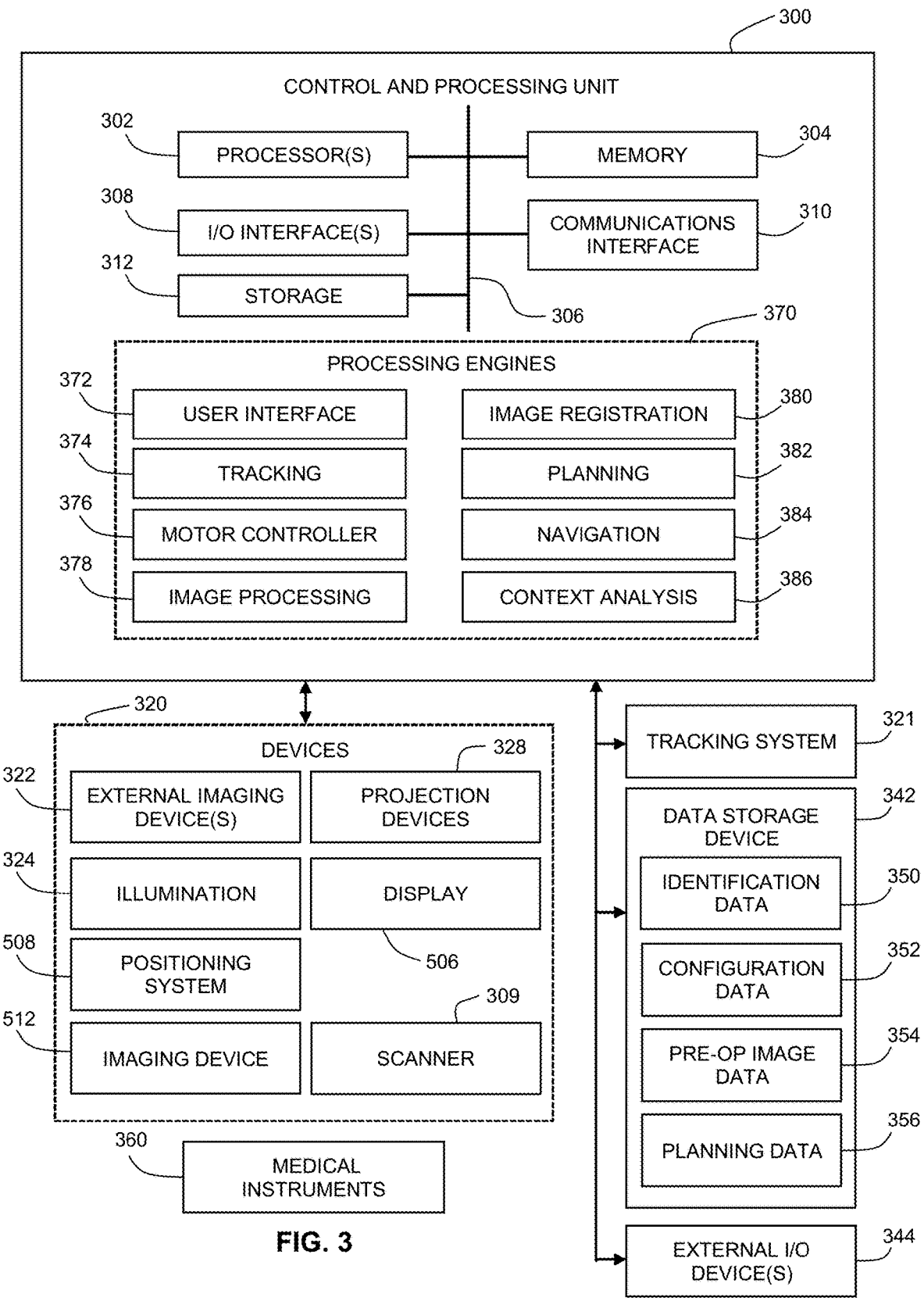
FIG. 3 is a block diagram illustrating an example control and processing system that may be used in the navigation system of FIG. 2.

In FIG. 3, a block diagram is shown illustrating a control and processing system 300 that may be used in the medical navigation system 205 shown in FIG. 2 (e.g., as part of the equipment tower). As shown in FIG. 3, in an example, the control and processing system 300 may include one or more processors 302, a memory 304, a system bus 306, one or more input/output interfaces 308, a communications interface 310, and a storage device 312. The control and processing system 300 may be interfaced with other external devices, such as a tracking system 321, data storage 342, and external user input and output devices 344, which may include, for example, one or more of a display, keyboard, mouse, sensors attached to medical equipment, foot pedal, and microphone and speaker. The data storage 342 may be any suitable data storage device, such as a local or remote computing device (e.g. a computer, hard drive, digital media device, or server) having a database stored thereon. In the example shown in FIG. 3, the data storage device 342 includes identification data 350 for identifying one or more medical instruments 360 and configuration data 352 that associates customized configuration parameters with one or more of the medical instrument(s) 360. The data storage device 342 may also include preoperative image data 354 and/or medical procedure planning data 356. Although the data storage device 342 is shown as a single device in FIG. 3, it will be understood that in other embodiments, the data storage device 342 may be provided as multiple storage devices.

The medical instruments 360 may be identifiable by the control and processing unit 300. The medical instruments 360 may be connected to and controlled by the control and processing unit 300, or the medical instruments 360 may be operated or otherwise employed independent of the control and processing unit 300. The tracking system 321 may be employed to track one or more medical instruments 360 and spatially register the one or more tracked medical instruments to an intraoperative reference frame. For example, the medical instruments 360 may include tracking markers such as tracking spheres that may be recognizable by a tracking camera. In one example, the tracking camera may be an infrared (IR) tracking camera. In another example, a sheath placed over a medical instrument 360 may be connected to and controlled by the control and processing unit 300.

The control and processing unit 300 may also interface with a number of configurable devices, and may intraoperatively reconfigure one or more of such devices based on configuration parameters obtained from the configuration data 352. Examples of devices 320, as shown in FIG. 3, include one or more external imaging devices 322, one or more illumination devices 324, a positioning system 508 (e.g., a robotic arm), an imaging device 512, one or more projection devices 328, one or more displays 506, and a scanner 309, which in an example may be a 3D scanner.

Exemplary aspects of the disclosure can be implemented via the processor(s) 302 and/or memory 304. For example, the functionalities described herein can be partially implemented via hardware logic in the processor 302 and partially using the instructions stored in the memory 304, as one or more processing modules or engines 370. Example processing modules include, but are not limited to, a user interface engine 372, a tracking module 374, a motor controller 376, an image processing engine 378, an image registration engine 380, a procedure planning engine 382, a navigation engine 384, and a context analysis module 386. While the example processing modules are shown separately in FIG. 3, in some examples the processing modules 370 may be stored in the memory 304 and the processing modules 370 may be collectively referred to as processing modules 370. In some examples, two or more modules 370 may be used together to perform a function. Although depicted as separate modules 370, the modules 370 may be embodied as a unified set of computer-readable instructions (e.g., stored in the memory 304) rather than distinct sets of instructions.

It is to be understood that the system is not intended to be limited to the components shown in FIG. 3. One or more components of the control and processing system 300 may be provided as an external component or device. In one example, the navigation module 384 may be provided as an external navigation system that is integrated with the control and processing system 300.

Some embodiments may be implemented using the processor 302 without additional instructions stored in memory 304. Some embodiments may be implemented using the instructions stored in memory 304 for execution by one or more general purpose microprocessors. Thus, the disclosure is not limited to a specific configuration of hardware and/or software.

In some examples, the navigation system 205, which may include the control and processing unit 300, may provide tools to the surgeon that may help to improve the performance of the medical procedure and/or post-operative outcomes. In addition to removal of brain tumours and intracranial hemorrhages (ICH), the navigation system 205 can also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, examples of the present disclosure may be applied to any suitable medical procedure.

Figure 4A:
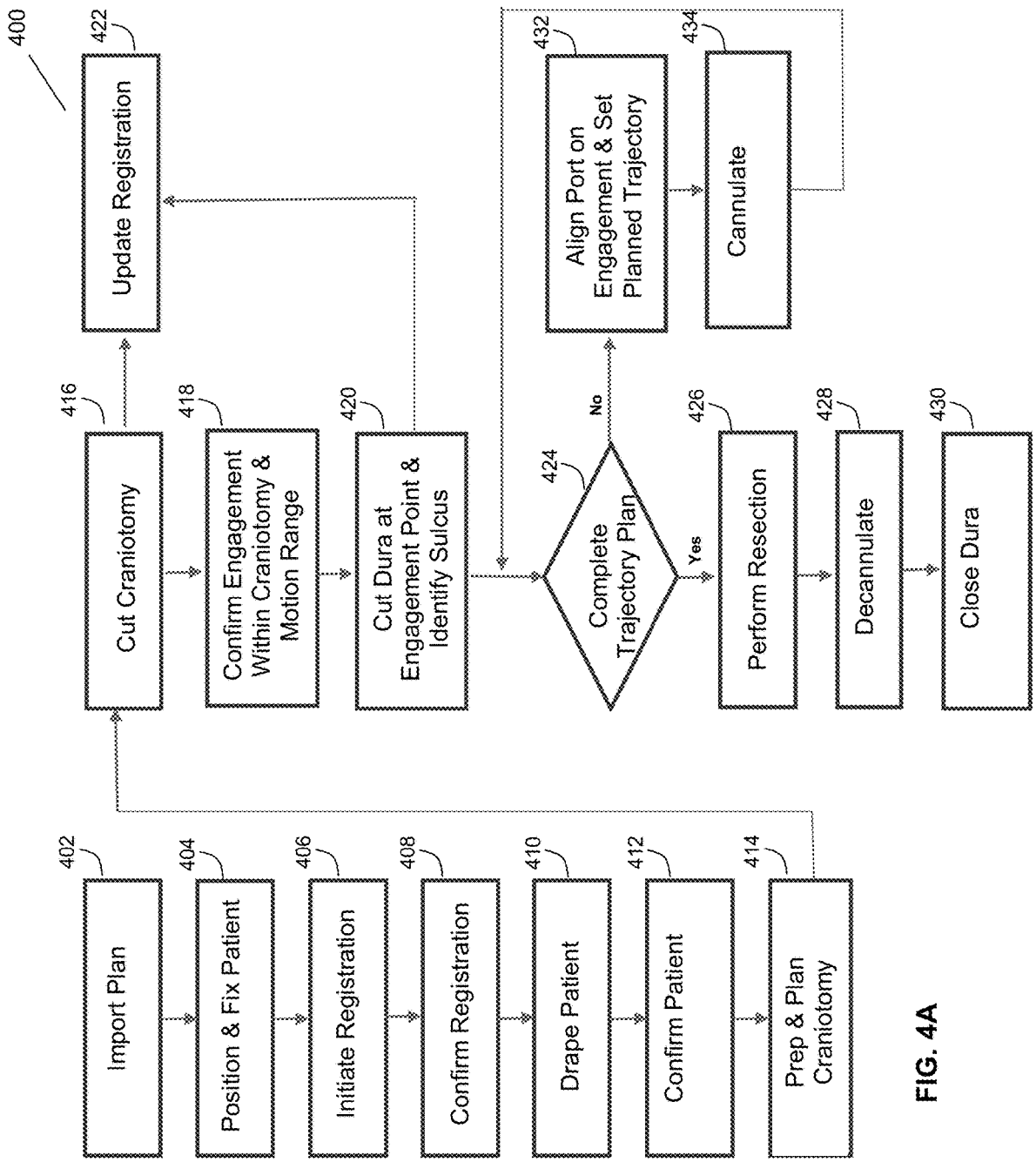
FIG. 4A is a flow chart illustrating an example method involved in a medical procedure that may be implemented using the navigation system of FIG. 2.

In FIG. 4A, a flow chart is shown illustrating an example method 400 of performing a medical procedure using a navigation system, such as the medical navigation system 205 described in relation to FIG. 2. At a first block 402, the surgical plan is imported.

Once the plan has been imported into the navigation system at the block 402, the patient is affixed into position using a body holding mechanism. The head position is also confirmed with the patient plan in the navigation system (block 404), which in one example may be implemented by the computer or controller forming part of the equipment tower of medical navigation system 205.

Next, registration of the patient is initiated (block 406). The phrase "registration" or "image registration" refers to the process of transforming different sets of data into one coordinate system. Data may include multiple photographs, data from different sensors, times, depths, or viewpoints. The process of "registration" is used in the present application for medical imaging in which images from different imaging modalities are co-registered. Registration is used in order to be able to compare or integrate the data obtained from these different modalities.

Those skilled in the relevant arts will appreciate that there are numerous registration techniques available and one or more of the techniques may be applied to the present example. Non-limiting examples include intensity-based methods that compare intensity patterns in images via correlation metrics, while feature-based methods find correspondence between image features such as points, lines, and contours. Image registration methods may also be classified according to the transformation models they use to relate the target image space to the reference image space. Another classification can be made between single-modality and multi-modality methods. Single-modality methods typically register images in the same modality acquired by the same scanner or sensor type, for example, a series of magnetic resonance (MR) images may be co-registered, while multi-modality registration methods are used to register images acquired by different scanner or sensor types, for example in magnetic resonance imaging (MRI) and positron emission tomography (PET). In the present disclosure, multi-modality registration methods may be used in medical imaging of the head and/or brain as images of a subject are frequently obtained from different scanners. Examples include registration of brain computerized tomography (CT)/MRI images or PET/CT images for tumor localization, registration of contrast-enhanced CT images against non-contrast-enhanced CT images, and registration of ultrasound and CT.

Figure 4B:
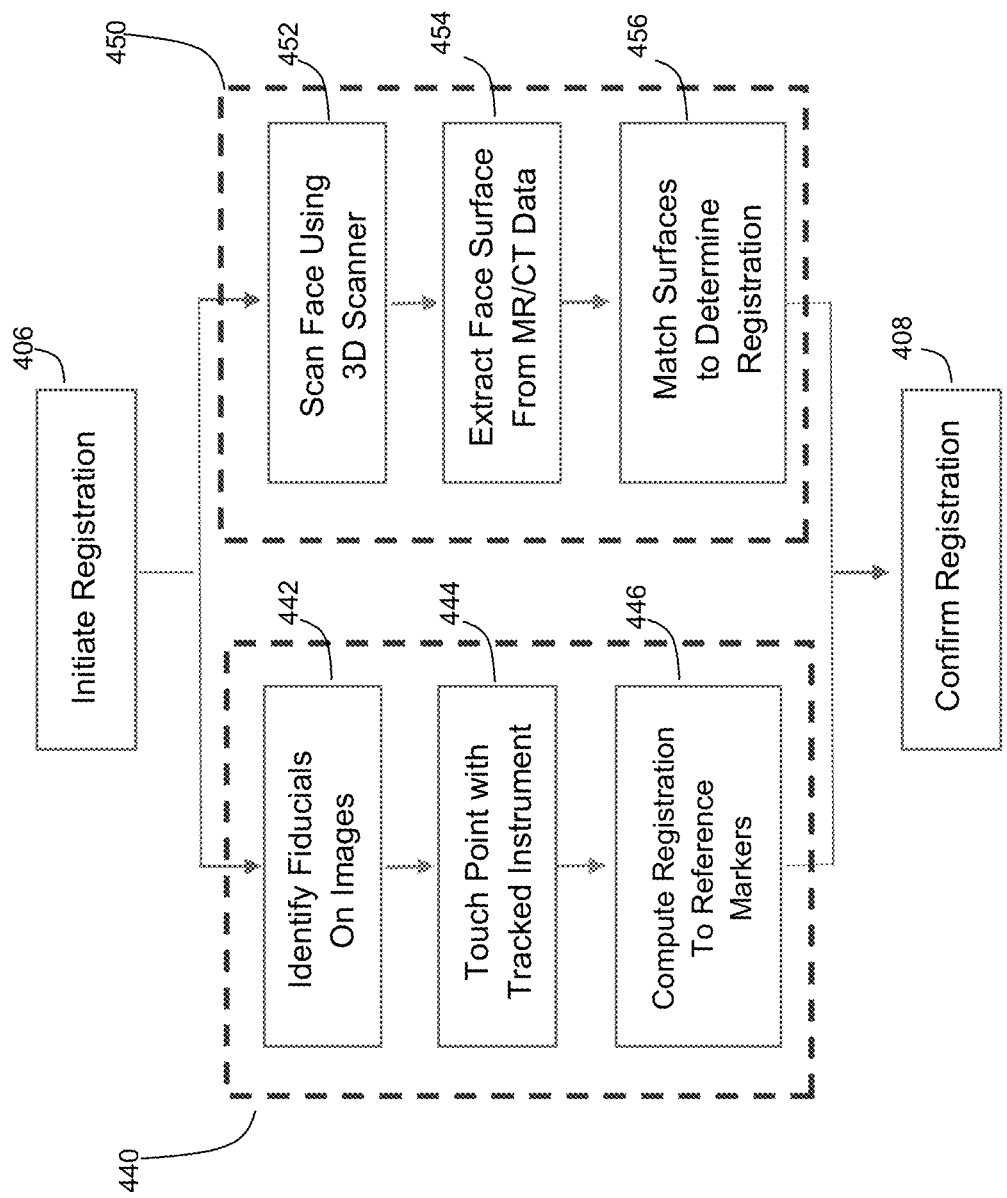
FIG. 4B is a flow chart illustrating an example method of registering a patient for a medical procedure as outlined in FIG. 4A.

In FIG. 4B, a flow chart is shown illustrating a method involved in registration block 406 as outlined in FIG. 4A, in greater detail. If the use of fiducial touch points (440) is contemplated, the method involves first identifying fiducials on images (block 442), then touching the touch points with a tracked instrument (block 444). Next, the navigation system computes the registration to reference markers (block 446).

Alternately, registration can also be completed by conducting a surface scan procedure (block 450). The block 450 is presented to show an alternative approach, but may not typically be used when using a fiducial pointer. First, the face is scanned using a 3D scanner (block 452). Next, the face surface is extracted from MR/CT data (block 454). Finally, surfaces are matched to determine registration data points (block 456).

Upon completion of either the fiducial touch points (440) or surface scan (450) procedures, the data extracted is computed and used to confirm registration at block 408, shown in FIG. 4B.

Referring back to FIG. 4A, once registration is confirmed (block 408), the patient is draped (block 410). Typically, draping involves covering the patient and surrounding areas with a sterile barrier to create and maintain a sterile field during the surgical procedure. The purpose of draping is to eliminate the passage of microorganisms (e.g., bacteria) between non-sterile and sterile areas. At this point, conventional navigation systems require that the non-sterile patient reference is replaced with a sterile patient reference of identical geometry location and orientation.

Upon completion of draping (block 410), the patient engagement points are confirmed (block 412) and then the craniotomy is prepared and planned (block 414).

Upon completion of the preparation and planning of the craniotomy (block 414), the craniotomy is cut and a bone flap is temporarily removed from the skull to access the brain (block 416). Registration data is updated with the navigation system at this point (block 422).

Next, the engagement within craniotomy and the motion range are confirmed (block 418). Next, the procedure advances to cutting the dura at the engagement points and identifying the sulcus (block 420).

Thereafter, the cannulation process is initiated (block 424). Cannulation involves inserting a port into the brain, typically along a sulci path as identified at 420, along a trajectory plan. Cannulation is typically an iterative process that involves repeating the steps of aligning the port on engagement and setting the planned trajectory (block 432) and then cannulating to the target depth (block 434) until the complete trajectory plan is executed (block 424).

Once cannulation is complete, the surgeon then performs resection (block 426) to remove part of the brain and/or tumor of interest. The surgeon then decannulates (block 428) by removing the port and any tracking instruments from the brain. Finally, the surgeon closes the dura and completes the craniotomy (block 430). Some aspects of FIG. 4A are specific to port-based surgery, such as portions of blocks 428, 420, and 434, but the appropriate portions of these blocks may be skipped or suitably modified when performing non-port based surgery.

When performing a medical procedure using a medical navigation system 205, as outlined in connection with FIGS. 4A and 4B, the medical navigation system 205 must acquire and maintain a reference of the location of the tools in use as well as the patient in 3D space. In other words, during a navigated neurosurgery, there needs to be a tracked reference frame that is fixed relative to the patient's skull. During the registration phase of a navigated neurosurgery (e.g., the step 406 shown in FIGS. 4A and 4B), a transformation is calculated that maps the frame of reference of preoperative MRI or CT imagery to the physical space of the surgery, specifically the patient's head. This may be accomplished by the navigation system 205 tracking locations of fiducial markers fixed to the patient's head, relative to the static patient reference frame. The patient reference frame is typically rigidly attached to the head fixation device, such as a Mayfield clamp. Registration is typically performed before the sterile field has been established (e.g., the step 410 shown in FIG. 4A).

Figure 5:
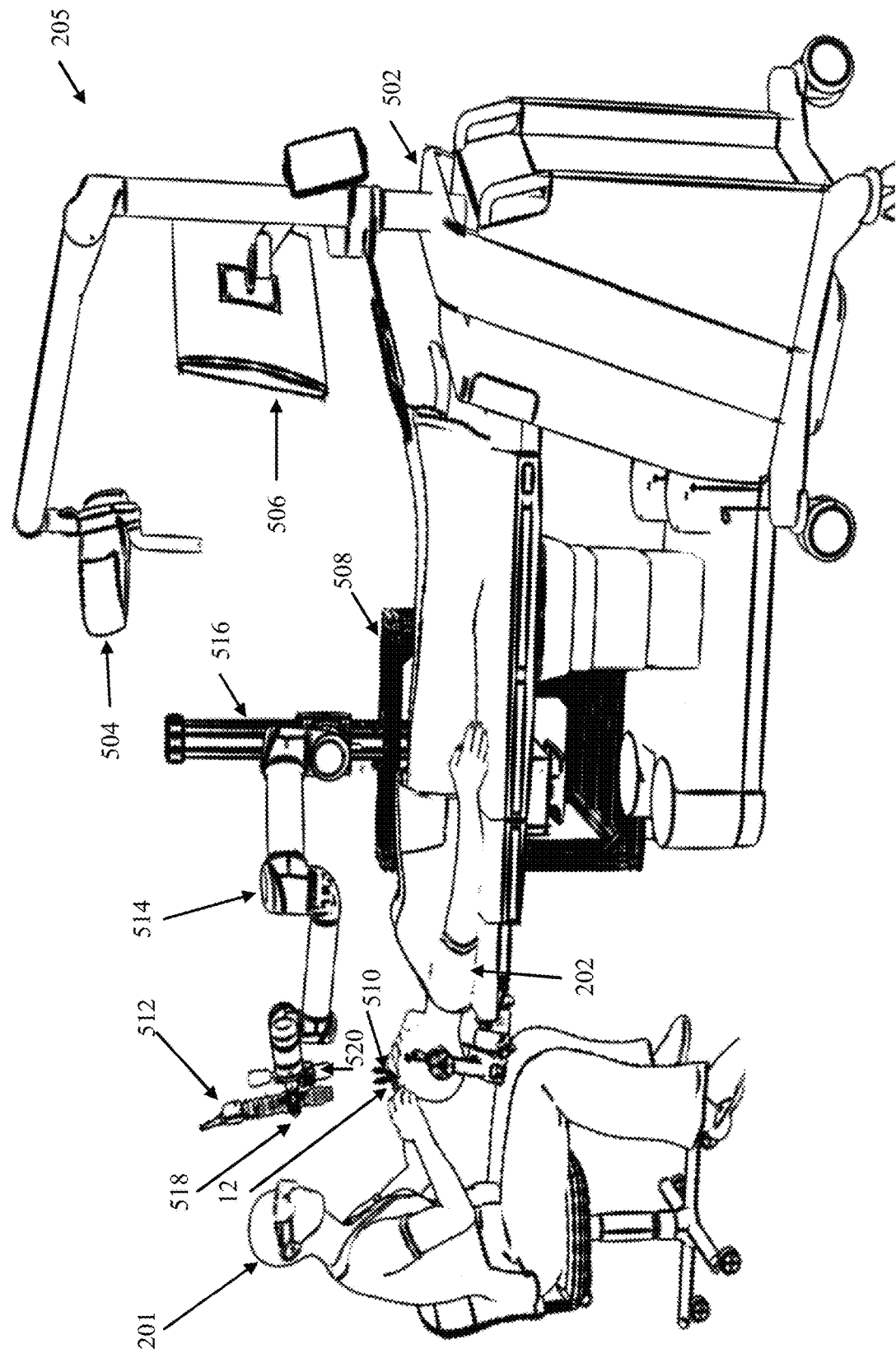
FIG. 5 is an example navigation system similar to FIG. 2, illustrating system components of an example system that may be used for acquiring a depth map of a site of interest.

FIG. 5 is a diagram illustrating components of an exemplary system, including the navigation system 205 of FIG. 2. Components of the navigation system 205 are described in greater detail. In the example of FIG. 5, the navigation system 205 includes an equipment tower 502, a tracking system 504, one or more displays 506, a positioning system 508 and tracking markers 510 used to track a medical instrument and/or an access port 12. The tracking system 504 may include an optical tracking device, tracking camera, video camera, 3D scanner, or any other suitable camera or scanner based system. In FIG. 5, the surgeon 201 is performing a tumor resection through the access port 12, using an imaging device 512 (e.g., a scope and camera) to view down the port at a sufficient magnification to enable enhanced visibility of the instruments and tissue. The imaging device 512 may be an external scope, videoscope, wide field camera, or an alternate image capturing device. The imaging sensor view is depicted on the visual display 506 which the surgeon 201 uses for navigating the port's distal end through the anatomical region of interest.

A positioning system 508, which in this example includes an automated mechanical arm 514 (also referred to simply as the automated arm 514), a lifting column 516 and an end effector 518, is placed in proximity to the patient 202. The lifting column 516 is connected to a frame of the positioning system 508. In the example of FIG. 5, the proximal end of the automated arm 514 is connected to the lifting column 516. In other examples, the automated arm 514 may be connected to a horizontal beam, which is then either connected to the lifting column 516 or directly to the frame of the positioning system 508. The automated arm 514 may have multiple joints, for example to enable 5, 6 or 7 degrees of freedom.

The end effector 518 is attached to the distal end of the automated arm 514. The end effector 518 may accommodate a plurality of instruments or tools that may assist the surgeon 201 in the procedure. In FIG. 5, the end effector 518 is shown as holding the imaging device 512, in this example an external scope and camera, however it should be noted that any alternate devices may be used with the end effector 518 such as a wide field camera, microscope and Optical Coherence Tomography (OCT), video camera, 3D scanner, or other imaging instruments, as well as devices other than an imaging device 512. In another example, multiple end effectors 518 may be attached to the distal end of the automated arm 514, and thus assist the surgeon 201 in switching between multiple modalities. For example, the surgeon 201 may want the ability to move between microscope, and OCT with stand-off optics. In some examples, it may be possible to attach a second end effector 518, for example a more accurate, but smaller range end effector (e.g., a laser based ablation system with micro-control).

In an example, the positioning system 508 receives as input information about the spatial position and orientation of the automated arm 514 and the port 12 (or other tracked object). The position and orientation of the port 12 may be determined by the tracking system 504 by detection of the tracking markers 510 on the port 12. The position and orientation of the automated arm 514 may be determined by the tracking system 504 by detection of tracking markers 510 on the automated arm 514, or based on position sensors on the automated arm 514, for example. The position and orientation of the end effector 518 may be determined based on the known position and orientation fo the end effector 518 relative to the automated arm 514. Further, it should be noted that the tracking markers 510 may be used to track both the automated arm 514 as well as the end effector 518 either collectively or independently. It should be noted that a wide field camera 520 is shown in the example of FIG. 5 and that it is connected to the imaging device 512 (e.g., external scope) and the two imaging devices 520, 512 together are held by the end effector 518. It should additionally be noted that although these are depicted together for illustration, either of the wide field camera 520 and the imaging device 512 could be utilized independently of the other, for example where the imaging device 512 is an external video scope that can be used independently of the wide field camera 520.

The positioning system 508 may compute the desired joint positions for the automated arm 514 so as to maneuver the end effector 518 mounted on the distal end of the automated arm 514 to a predetermined spatial position and orientation relative to the port 12. This predetermined relative spatial position and orientation may be designated as the "Zero Position" where the imaging device 512 and the port 12 are axially aligned.

Further, the positioning system 508, the tracking system 504, the automated arm 514, and tracking markers 510 may form a feedback loop. This feedback loop may work to keep the distal end of the port 12 (which may be located inside the patient's brain during the procedure) in constant view and focus of the imaging device 512 (e.g., where the end effector 518 holds the imaging device 512), as the position of the port 12 may be dynamically manipulated by the surgeon 201 during the procedure. The positioning system 508 may also include an input mechanism, such as a foot pedal, for use by the surgeon 201 to instruct the automated arm 514 to automatically align the end effector 518 (e.g., holding a videoscope) with the port 12.

Figure 6:
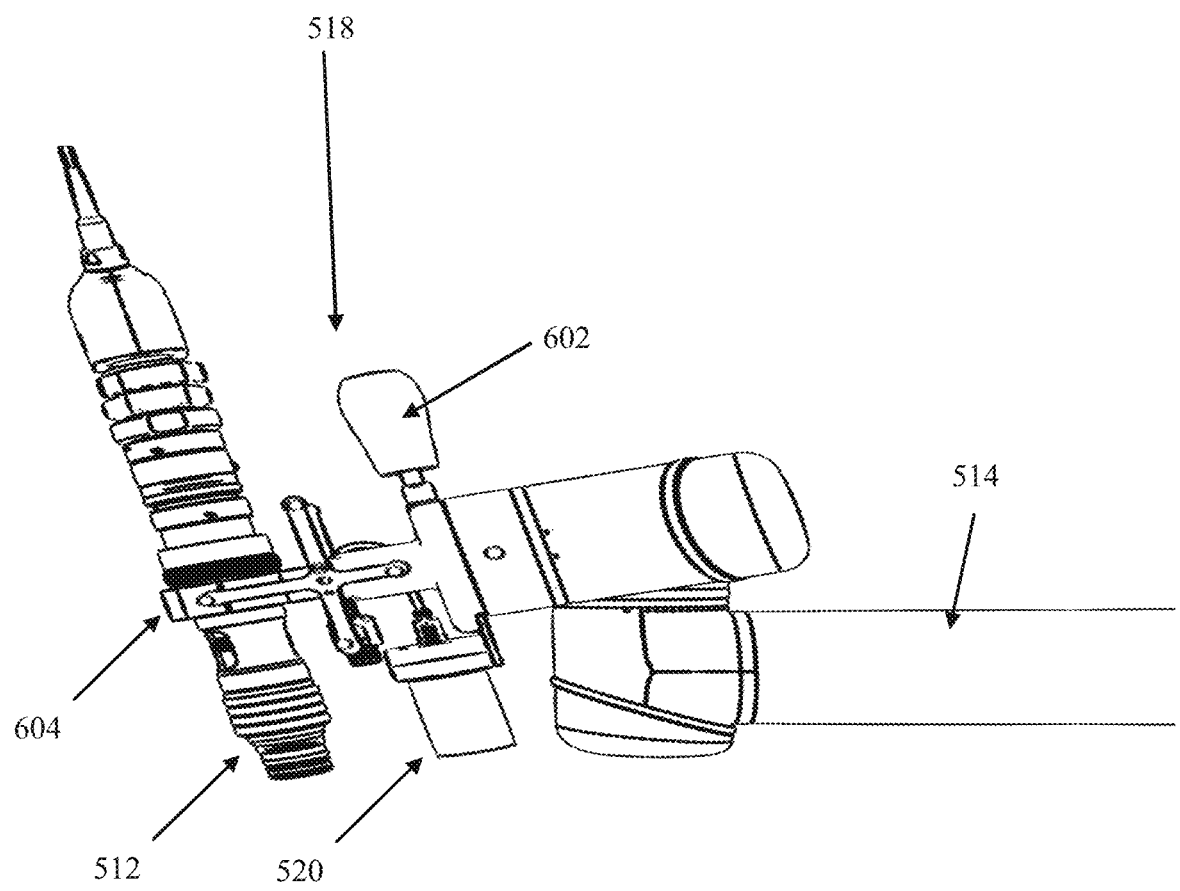
FIG. 6 is perspective drawing illustrating an example end effector holding a camera.

In FIG. 6, an example of the end effector 518 is shown attached to the automated arm 514. The end effector 518 in this example includes a handle 602 and a scope clamp 604. The scope clamp 604 holds the imaging device 512. The end effector 518 also has the wide field camera 520 attached thereto, which in one example could be a still camera, a video camera, or 3D scanner and which may be used to monitor muscles of the patient for movement, tremors, or twitching, for example.

A depth map may be generated in various ways. Some examples are described in PCT Application No. PCT/CA2015/050651, and in PCT Application No. PCT/CA2016/050189, both incorporated herein by reference in their entirety.

The depth information may be obtained using any suitable depth detector. For example, depth information may be determined based on the depth of field (DOF) (also referred to as focus range) of the imaging device 512. The DOF may be defined as the distance between the nearest and farthest elements in the field-of-view (FOV) of the imaging device 512 that appear in focus in a captured image. In some examples, the DOF and the midpoint between the "near" and "far" edges (e.g., the working distance) are controlled by the optics of the scope system, such as the imaging device 512, and by determining what sections of an image are in focus, where the distance or depth of those sections from the scope can be extracted or calculated. The control and processing unit 300 may control the imaging device 512 to change the working distance and capture images at different working distances. The control and processing unit 300 may then analyze the change in image focus over the different images and thus calculate depth information for different portions of the image. In this way, a depth map may be generated, which maps out depth information over the entire image. Narrowing the DOF may be used to increase the resolution in depth data.

In some examples, the 3D scanner 309 may instead be used to capture data about a 3D surface. The 3D scanner 309 may provide depth information directly to the control and processing unit 300 (e.g., without requiring further calculations to obtain depth information).

Depth information may be acquired over a site of interest, such as human tissue, for example a portion of a patient that is the subject of a medical procedure, for example brain tissue. Generally, depth information may be obtained for each pixel in an image captured by the imaging device 512. This may be equally the case whether the captured image is static or a video image. The depth information may be used to generate a 3D point cloud and/or a 3D surface contour, for example.

Figure 7A:
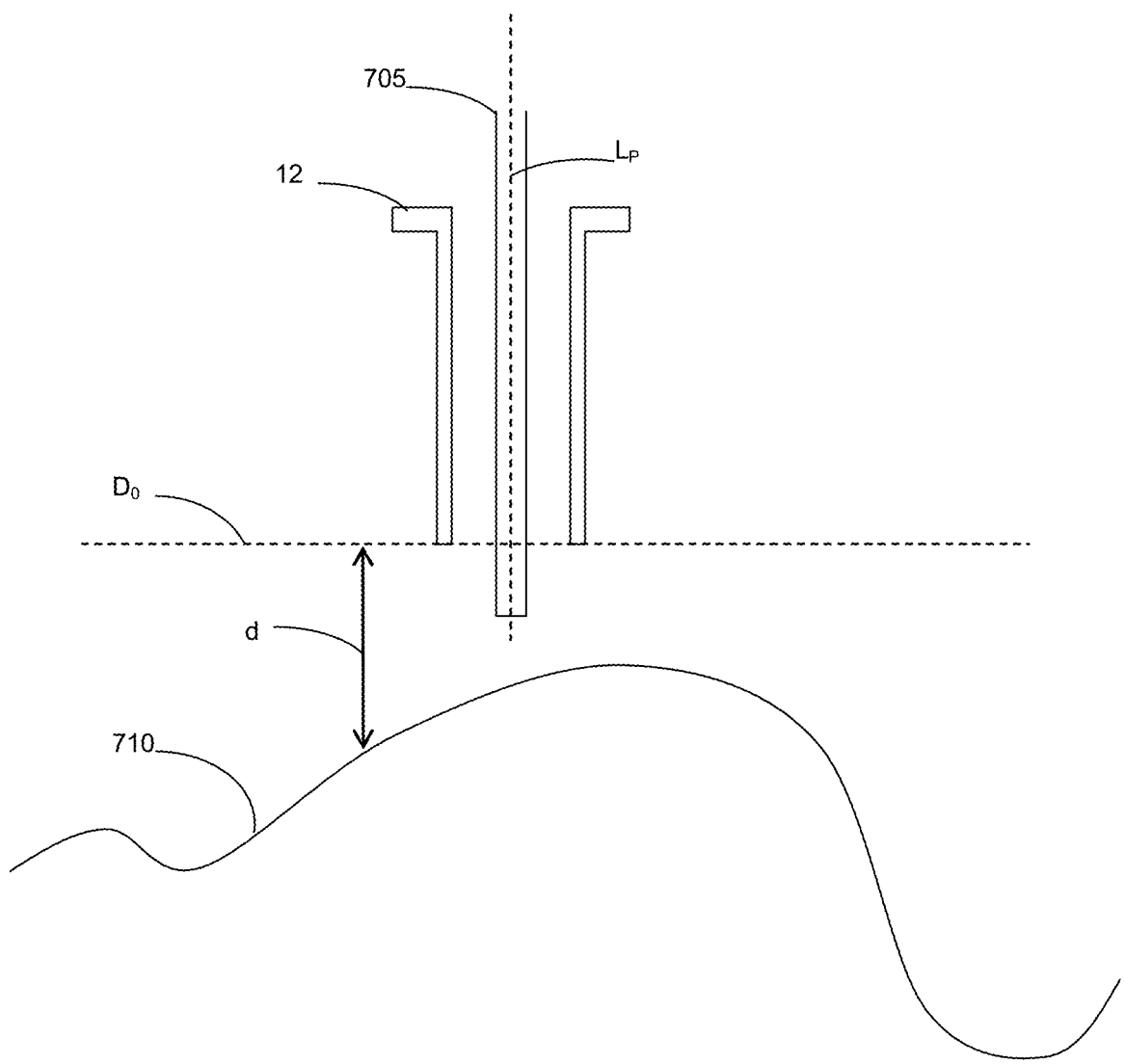
FIGS. 7A and 7B are simplified diagrams illustrating example instruments at sites of interest.

FIG. 7A is a simplified diagram illustrating how depth information for a surface (e.g., a tissue surface of at the site of interest) may be measured. FIG. 7A shows the access port 12 providing access for a medical instrument 705 (e.g., a medical pointer, an ablation catheter, a surgical probe, a medical pointer, a suction tool or a surgical tool; in some examples, the access port 12 itself may be considered to be the medical instrument) towards a surface 710 that has variations in depth. The port 12 has a longitudinal axis $L_P$. As discussed above, the imaging device 512 is kept aligned with the port 12 (e.g., using tracking information from the tracking system 504) such that the line-of-sight of the imaging device 512 is along the longitudinal axis $L_P$ of the port 12. Depth information of the surface 710 may be determined as a depth value relative to a defined zero-depth plane $D_0$. In the example of FIG. 7A, the zero-depth plane $D_0$ is shown to be defined by the distal end of the port 12. In other examples, the zero-depth plane $D_0$ may be defined by another reference point, for example relative to the distal end of the imaging device 512 (e.g., the end of an exoscope). Depth information for a given portion of the surface 710 may then be measured as the perpendicular distance d relative to the zero-depth plane $D_0$. The zero-depth plane $D_0$ may be defined by the surgeon intra-operatively and dynamically. For example, the surgeon may wish to know depth values relative to the distal end of the access port 12, relative to the distal tip of the medical instrument 705, or relative to some other fixed reference point.

Figure 7B:
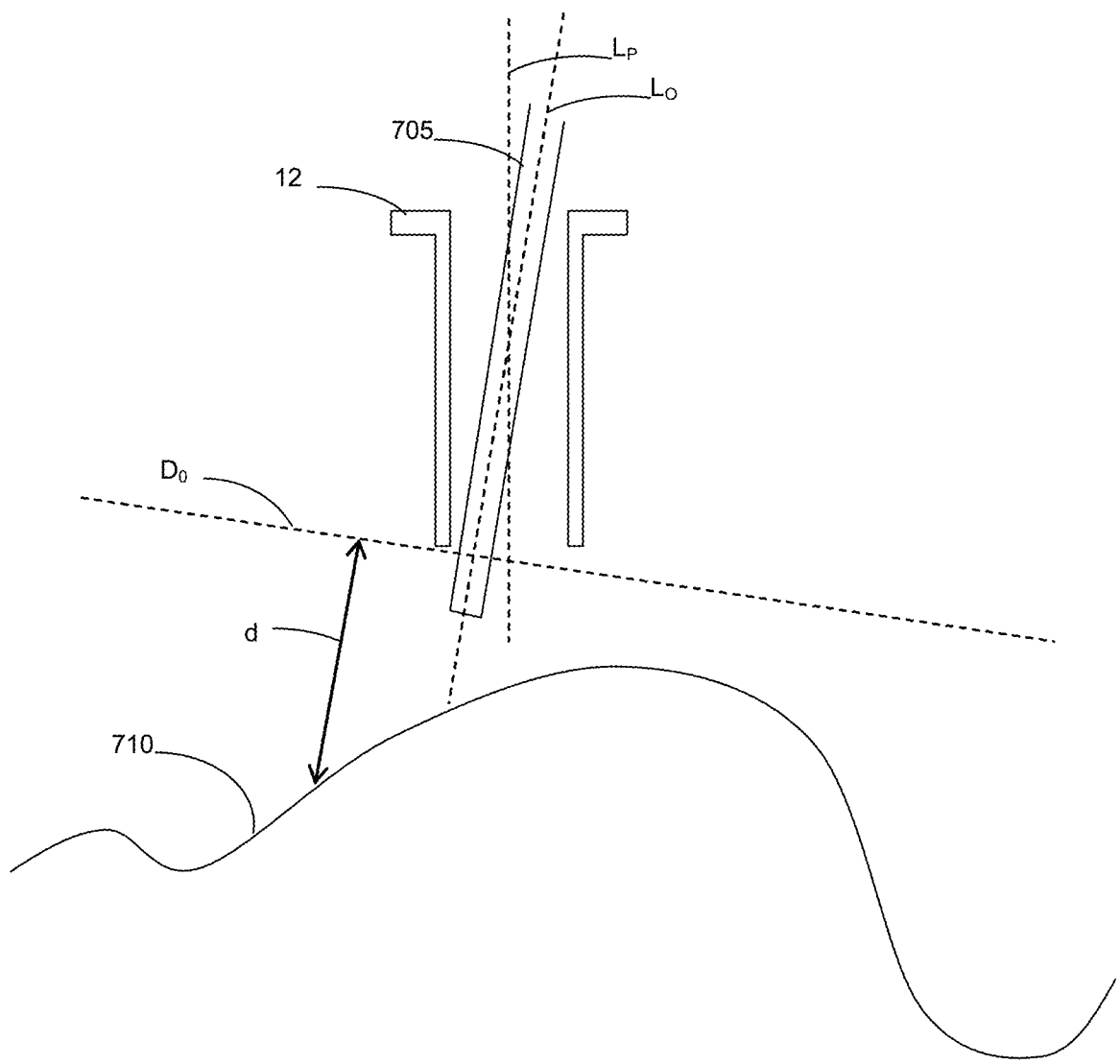

In FIG. 7A, the medical instrument 705 is shown aligned with the longitudinal axis $L_P$ of the port 12. However, the longitudinal axis of the medical instrument 705, referred to as the operational axis $L_O$, may be at an angle relative to the port 12, for example as shown in FIG. 7B. In such a scenario, it may be useful to define the zero-depth plane $D_0$ based on the operational axis $L_O$ of the medical instrument 705. For example, the zero-depth plane $D_0$ may be defined using the operational axis $L_O$ as the normal, as shown in FIG. 7B. The zero-depth plane $D_0$ may also be shifted to coincide with the depth of the distal tip of the medical instrument 705 (not shown).

In the present disclosure, depth data that represents depth information over the general site of interest (e.g., the surface 710) may be referred to as general depth data. General depth data provides depth information that is not dependent on the medical instrument 705. In the present disclosure, depth data that relates a depth of the medical instrument 705 to variations in depth over the site of interest (e.g., the surface 710) may be referred to as relative depth data. Relative depth data is dependent on the position and orientation of the medical instrument 705. The position and orientation of the medical instrument 705 may be determined using tracking information from the tracking system 504 that is tracking markers on the medical instrument 705.

Figure 8A:
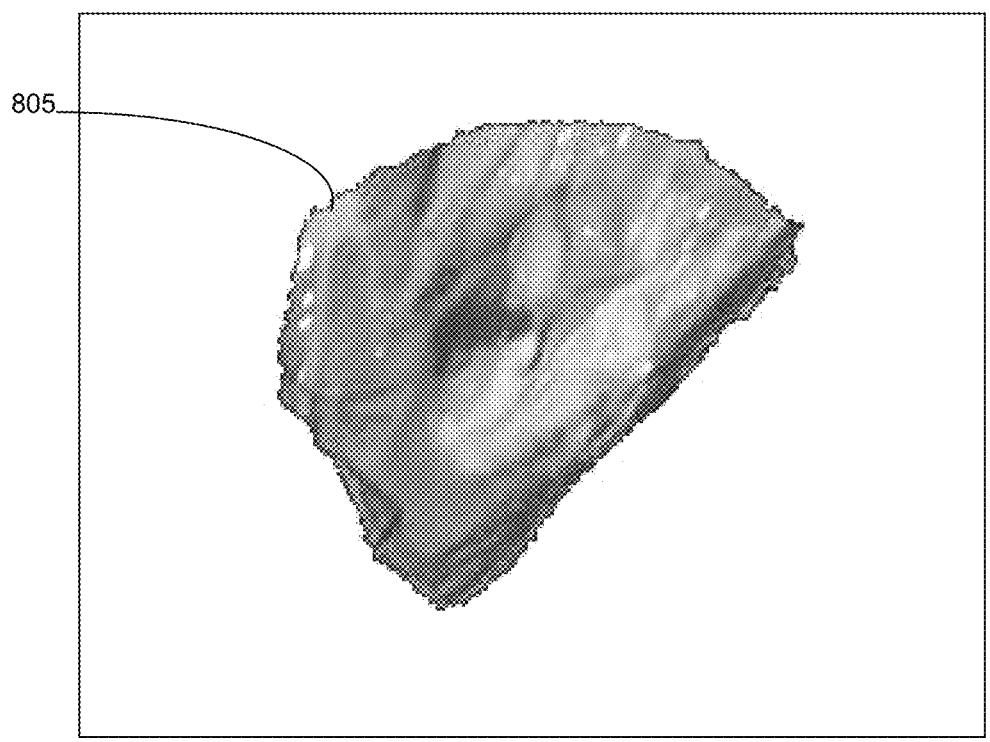
FIGS. 8A and 8B shown images of an example 3D topographic map representing depth information for a site of interest.
Figure 8B:
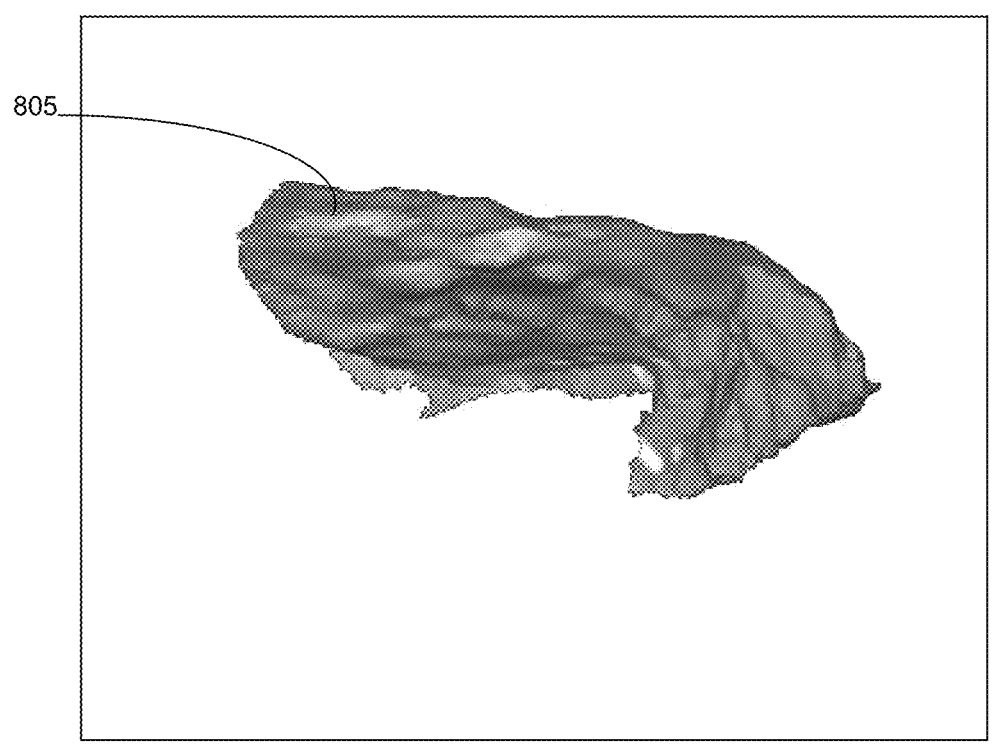

General depth data may be displayed as a 3D topographic map, for example as shown in FIG. 8A. The 3D topographic map 805 may be a 3D rendering displayed on a 2D display (e.g., the one or more displays 506 of the navigation system 205). The 3D topographic map may be displayed overlaid on a static or video 2D image (e.g., as captured by the imaging device 512). The surgeon or other user may interact with the 3D topographic map 805, for example using an input device such as a mouse. For example, the 3D topographic map 805 may be rotated in order to obtain better depth perception, view otherwise obscured 3D depth data and/or to obtain depth cues such as motion parallax. For example, FIG. 8B shows the 3D topographic map 805 of FIG. 8A after rotation (e.g., in response to user input). In the examples of FIGS. 8A and 8B, the 3D topographic map 805 is not overlaid on a captured image.

In some examples, indicators may be shown on the 3D topographic map 805 to indicate, for example, the location of a tracked instrument or tissue of interest (e.g., a tumour) relative to the surface. The 3D topographic map 805 may be presented in grayscale, or may be coloured. Colouring of the 3D topographic map 805 may be designed to match colouring of the actual tissue surface, or may be designed to encode additional information, for example depth information or tissue type information.

In some examples, the topographic information may be presented as a 3D collection of points, also referred to as a point cloud (not shown). The points in the point cloud may be presented in grayscale, or may be coloured similarly to that described above.

Figure 9A:
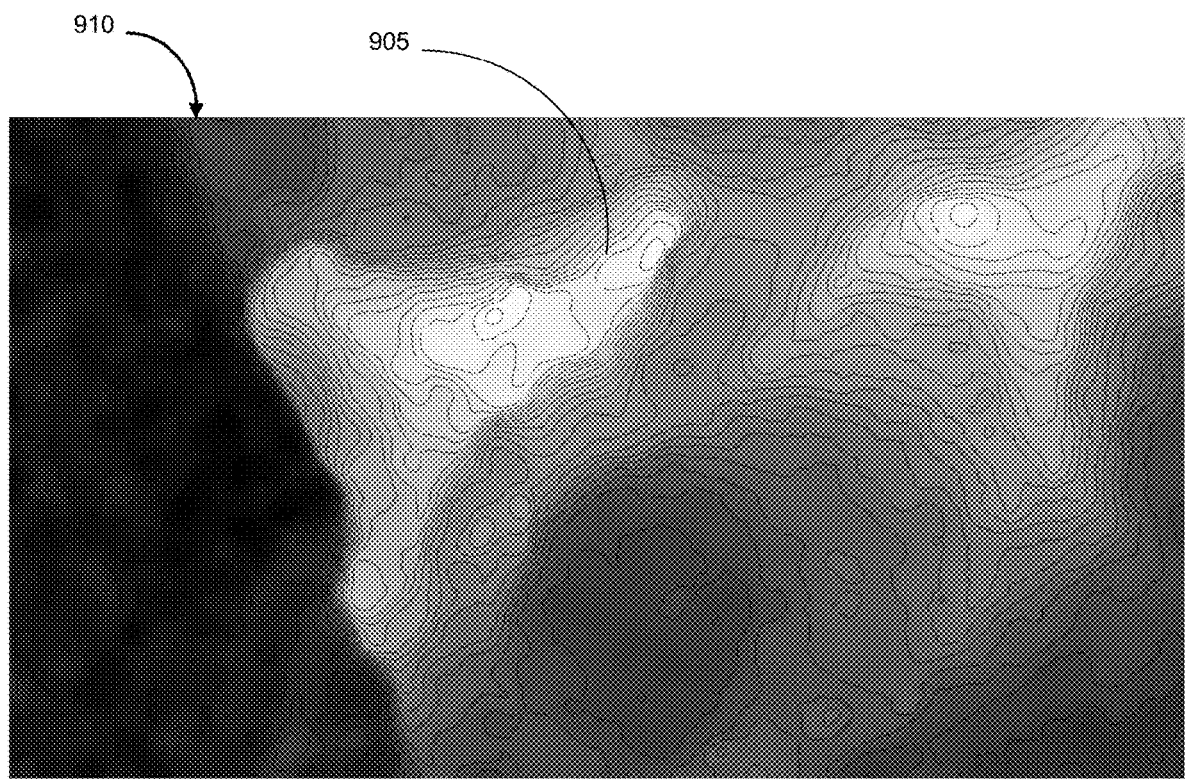
FIG. 9A is an image of an example display of contour lines overlaid on a captured image of a site of interest.

Depth data may also be displayed as a set of contour lines, for example as shown in FIG. 9A. In FIG. 9A, the contour lines 905 are displayed overlaid on a captured 2D image 910, which may be a static image or a video image (e.g., a static or video 2D image obtained using the imaging device 512, such as an exoscope) of the site of interest. Contour lines 905 may also be displayed overlaid on a 3D rendering of the site (e.g., overlaid on the topographic map 805 described above). Where the captured image 910 is a video image, the contour lines 905 are redrawn (and recalculated where necessary) to match changes in the video image.

Indicators (e.g., symbols or numbers) may be provided at each contour line 905 to indicate the depth of each contour line 905. The contour lines 905 may be presented in different colors, thicknesses and/or line styles to indicate depth information. The depth data may also be displayed in the form of a semi-transparent color overlay over the 2D or 3D image. Different colors may be predefined (e.g., by default or by the surgeon) for specific depth ranges.

The contour lines 905 may represent general depth data, showing depth information over the image independently of any medical instrument. The surgeon or other user may provide input (e.g., using an input device such as a mouse) on a user interface (e.g., provided on the same or different display 506) to select the way the contour lines 905 are displayed (e.g., changing among the different visual representations described above). The surgeon may also select (e.g., by interacting with a slider or other interactive input element provided in the user interface) the depths or depth ranges for which contour lines 905 are displayed. For example, the surgeon may adjust a slider in a user interface such that contour lines are displayed only for depths of 1-1.5 cm. Contour lines 905 outside of the selected depths or depth ranges may be hidden. Alternatively or additionally, portions of the image corresponding to tissues at the selected depths or depth ranges may be visually distinguished from portions outside of the selected depths or depth ranges. For example, highlighting or other colouration may be used to emphasize or de-emphasize certain portions of the image; and/or portions of the image outside of the selected depths or depth ranges may be blurred.

Figure 9B:
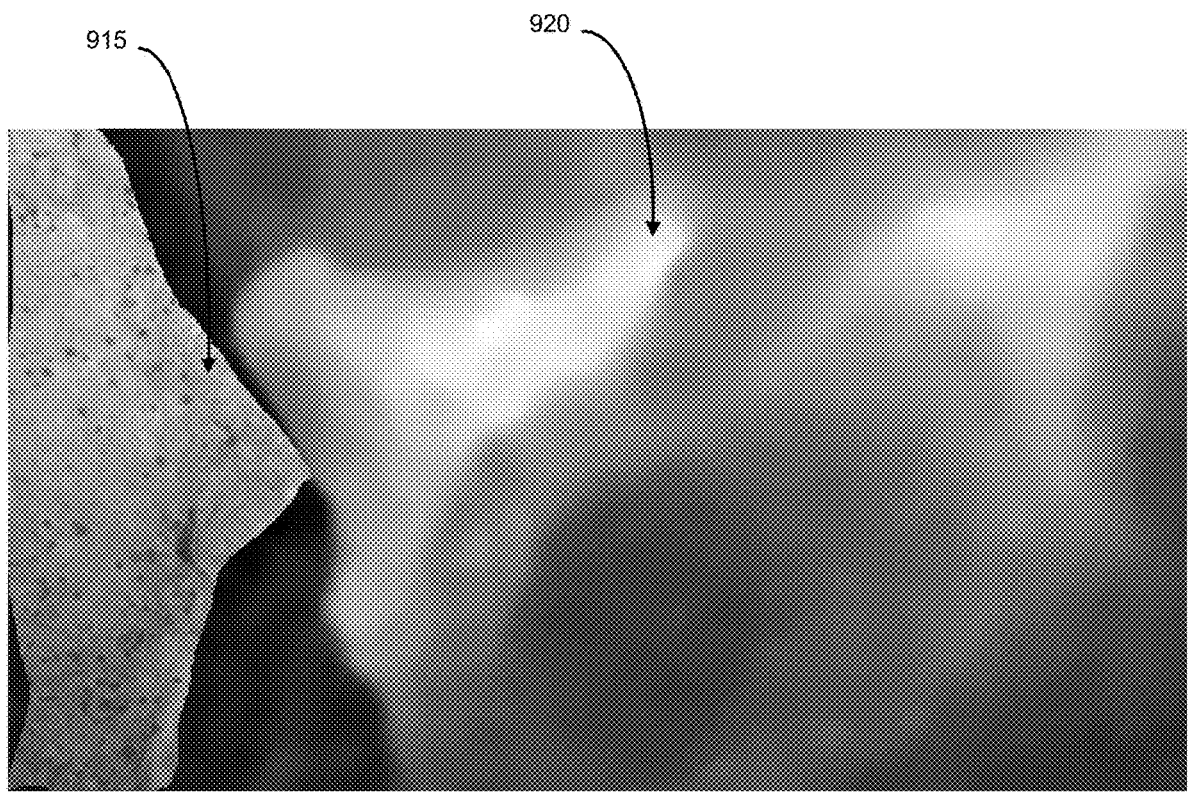
FIG. 9B is an image of an example of selective blurring of a captured image.

FIG. 9B shows an example image in which portions of the image have been blurred. The blurring may be a visual modification of a captured static or dynamic 2D image (e.g., a static or video 2D image obtained using the imaging device 512, such as an exoscope) of the site of interest. The image portions that are in focus 915 correspond to tissues at a selected depth range, while other image portions that are blurred 920 correspond to tissues outside of the selected depth range. The user interface may provide an option to dynamically change the selected depth range, and the blurring of the image may change to blur different portions of the image accordingly.

The contour lines 905 may also be used to represent relative depth data. For example, the display may show only contour lines 905 corresponding to a depth or depth range close to the depth of the instrument tip. Image portions may be visually modified, for example by colouration or blurring as discussed above, to visually distinguish those image portions within the depth range of the instrument tip. As the instrument tip moves to different depths, the contour lines and/or visual modification may change accordingly. This selective display of contour lines and/or selective blurring of the image, relative to the depth of the instrument tip, may be provided in place of the user selection using a user interface. For example, where the user interface provides a slider for user selection of a depth range, as described above, the slider may automatically move according to the depth of the instrument tip.

The relative depth data may also provide depth information relative to not only the location of the tip of the medical instrument, but also relative to the orientation of the medical instrument. By default, the general depth data may represent depth information measured relative to a zero-depth plane $D_0$ defined by the viewpoint of a camera along the access port (e.g., as shown in FIG. 7A). However, the medical instrument may be positioned at an angle relative to the access port (e.g., as shown in FIG. 7B). As discussed above, the position and orientation of the medical instrument may be determined intra-operatively by the tracking system 504, for example using tracking markers as described above. The relative depth data may represent depth information measured relative to a zero-depth plane $D_0$ defined by of the instrument's operational axis $L_O$.

Figure 10B:
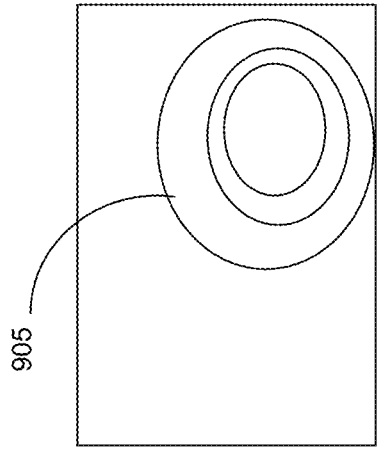
FIGS. 10A and 10B are diagrams illustrating the calculation of contour lines relative to an instrument.
Figure 10B:
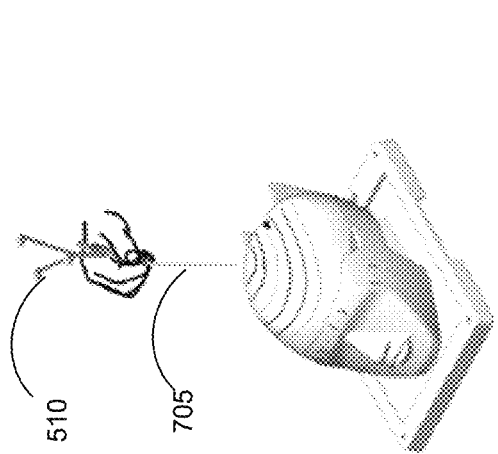
Figure 10A:
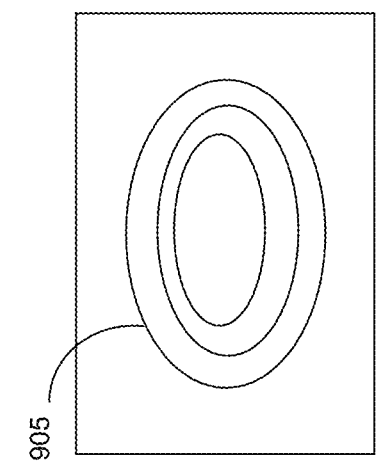
Figure 10A:
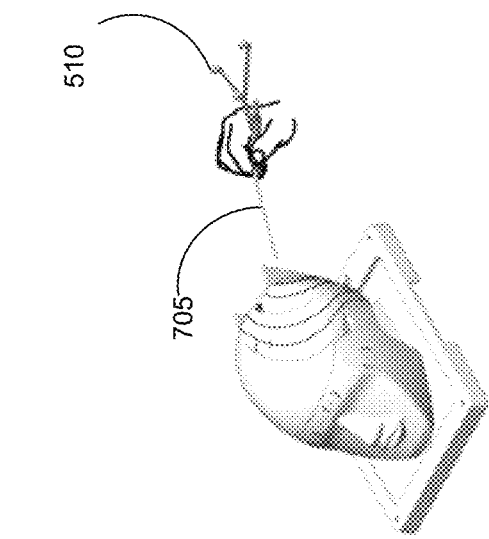

This is illustrated in FIGS. 10A and 10B, in which the medical instrument 705 is a fiducial pointer with tracking markers 510. FIGS. 10A and 10B show the use of a pointer on a model head, for simplicity, however relative contour lines may be similarly calculated for other medical instruments in an actual surgical site. In FIG. 10A, the medical instrument 705 is positioned vertically above the skull. The orientation and position of the medical instrument 705 may be tracked by the tracking system 504 of the navigation system 205, using the tracking markers 510. The depth variations of the site of interest may be calculated relative to the determine position and orientation of the medical instrument 705. This relative depth data may be displayed as contour lines 905 over the image 910 (e.g., similar to FIG. 9A), shown in a simplified form at the top of FIG. 10A. When the medical instrument 705 is moved to a different position and/or orientation, as shown in FIG. 10B, the relative depth data is recalculated accordingly. The recalculated relative depth data may be displayed as contour lines 905 over the image 910, shown in a simplified form at the top of FIG. 10B. It should be noted that although the site of interest has not changed, the contour lines 905 are different between FIGS. 10A and 10B, corresponding to the different position and orientation of the medical instrument 705.

The depth data may also be provided to the surgeon using non-visual output, in addition to or alternative to the visual output described above. For example, depth data may be communicated to the surgeon via audio and/or haptic output modalities as well. Non-visual output may be provided using any suitable visualization aid devices, such as devices developed to assist those with sight impairment.

Audio output may be provided by an audio output device, such as a speaker. General or relative depth data may be provided to the surgeon by encoding depth values in changes in timbre, pitch and/or amplitude of sounds.

Audio output may encode the depth value at specific spatial locations of an image. Spatial position in the image may be encoded, for example in the pitch and timbre of the sound. Where the audio output is capable of stereo output (e.g., stereo speakers), different speakers may output audio feedback for different portions of the image. For example, a left speaker may output audio feedback related to a left side of the image, while a right speaker may output audio feedback related to a right side of the image.

Figure 11:
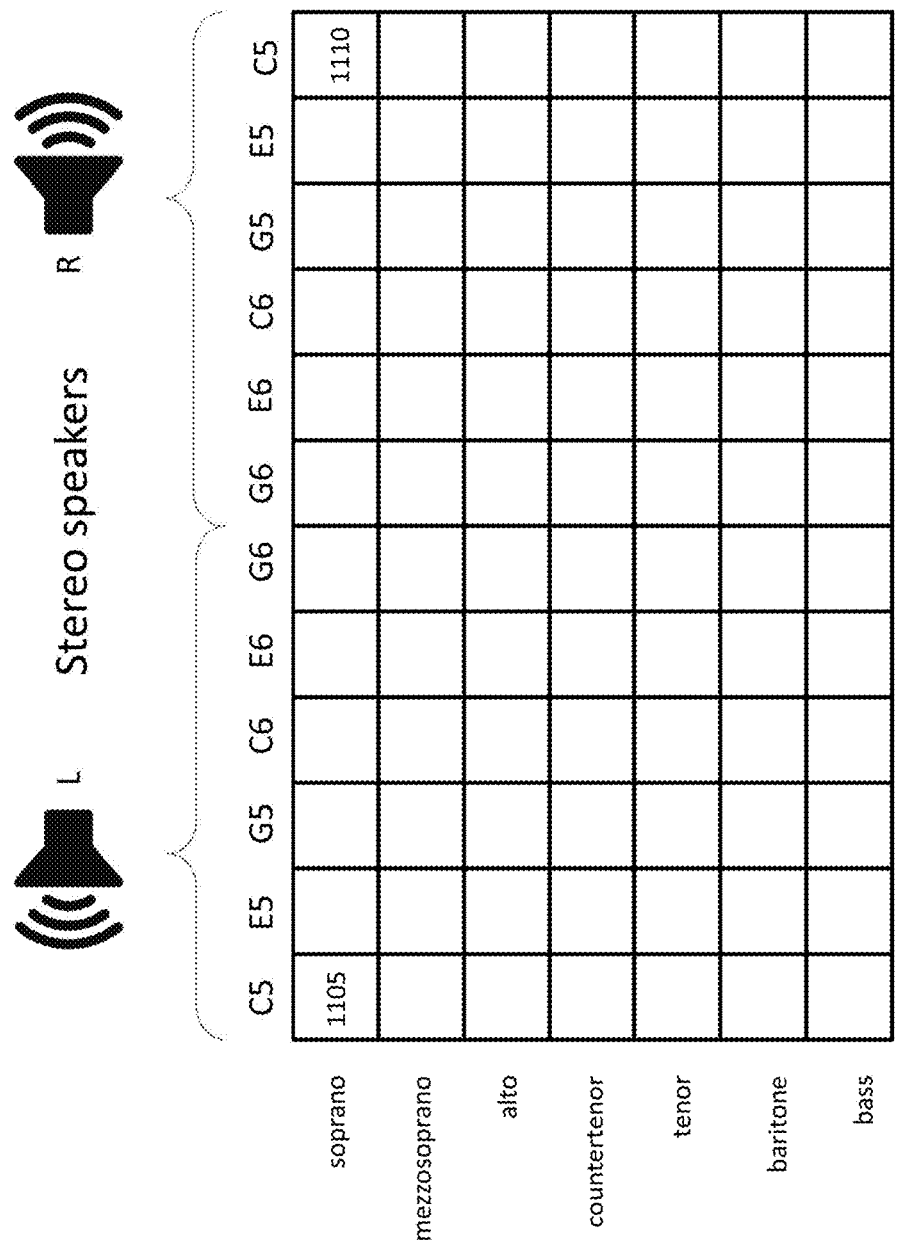
FIG. 11 is a diagram representing audio encoding of image portions.

FIG. 11 illustrates a simple example of how such encoding may be implemented. In the example of FIG. 11, 84 image portions are defined, according to a 7×12 grid. The vertical location of an image portion may be encoded by a distinct timbre (e.g., different voice types or different musical instruments), while the horizontal location of an image portion may be encoded by different pitches (e.g., using the musical notes of C, E and G in different octaves). Furthermore, output from left and right stereo speakers may be used to encode respective left and right sides of the image, thus enabling the same pitch to be repeated on left and right sides (which may allow for doubling the number of horizontal locations that can be encoded using a given set of different pitches). For example, a defined area in an upper left corner 1105 of the image may be encoded as an audio output from the left speaker with a pitch in the musical note of C5, with the timbre of a soprano voice. Similarly, the upper right corner 1110 may also be encoded with the timbre of a soprano voice and pitch C5, similar to the upper left corner, but the audio output would be provided from a right speaker.

In some examples, multiple audio output devices may be placed at different locations relative to the surgeon, and the audio output may be adjusted such that the surgeon hears the sound coming from a location corresponding to the image portion. For example, a sound that is heard to come from in front of the surgeon may correspond to an image portion in the center of the image; while a sound that is heard to come from the left of the surgeon may correspond to an image portion on the left side of the image. In some examples, instead of locating audio output devices around the surgeon, the surgeon may instead wear headphones that are capable of providing a surround sound output.

The depth value in that defined area may be encoded in the amplitude of the sound. For example, the sound may be louder for a higher depth value. In some examples, when an image portion corresponds to tissues outside of a user-selected depth range, there may be no audio output provided for that image portion.

Relative depth data may be outputted as audio output representing the depth of the tip of the medical instrument. For example, the audio output may be a sound of increasing pitch, increasing amplitude and/or increasing frequency of timbres as the tip of the medical instrument increases/decreases in depth. In some examples, where different image portions are encoded by different pitch and/or timbre of sound, the audio output may be a series or chorus of sounds for only the image portions corresponding to tissues at the depth of interest (e.g., corresponding to the depth of the tip of the medical instrument). The audio output may also be different pitches and/or timbres of sound indicating the image portion where the instrument tip is located. Where stereo output is provided, audio output may be provided via a left or right speaker to indicate whether the instrument tip is located in the left or right portion of the image, for example.

The audio output may be configured to assist the surgeon in aligning the medical instrument with a desired position and orientation (e.g., aligned with a planned surgical trajectory). For example, the audio output may provide a sound that varies (e.g., changing in amplitude, pitch and/or timbre) depending on how well the medical instrument is aligned with the desired position and orientation. In another example, the audio output may include a first pitch representing the desired position and orientation and a second pitch that changes based on the tracked position and orientation of the medical instrument. When the medical instrument is nearing the desired position and orientation, the two pitches may be close in frequencies, giving rise to an interference beat. When the two pitches match, the surgeon knows that the medical instrument is at the desired position and orientation.

For general depth data, the audio output may be provided as a series of sounds, where the order of the sounds corresponds to a predefined order for each image portion. For example, a series of sounds may be played as the image is traversed from upper left corner to lower right corner, each sound encoding the depth value as well as the respective image portion. The audio output may also be provided as a chorus of sounds, where the sounds encoding the depth value for each image portion are all outputted together. Similarly to visual output, audio output of depth data may be provided only for certain user-selected depths or depth ranges. For example, the audio output may include only sounds representing those image portions corresponding to the user-selected depths or depth ranges.

To avoid confusion, in some examples the audio output may be switched between general depth data and relative depth data, but not both at the same time.

Haptic output may be provided via an output device worn by the surgeon (e.g., on the arm, hand or tongue). The depth data may be encoded in a pressure signal (e.g., encoded in amplitude and/or frequency of a vibration). For example, greater depth values may be represented by greater pressure signals. The pressure signal may be spatially defined, corresponding to a respective image portion.

General depth data may be outputted as a pressure map corresponding to the image, where the pressure signal in a particular portion of the pressure map represents the depth value for a corresponding portion of the image. Similarly to visual output, haptic output of depth data may be provided only for certain user-selected depths or depth ranges. For example, the haptic output may include vibrations corresponding only to those image portions corresponding to the user-selected depths or depth ranges.

Relative depth data may be outputted as a haptic signal representing the depth of the tip of the medical instrument. For example, a haptic output device may vibrate at a higher frequency when the tip of the medical instrument is at a greater depth relative to the site of interest. The relative depth data may also be outputted as vibrations corresponding only to those image portions at or near the depth of the instrument tip, for example.

Other forms of visual output may be provided, using output devices other than a display screen. For example, a light (e.g., a LED) or other visual indicator may be provided on the medical instrument (or elsewhere in the system), and this visual indicator may be activated (e.g., LED turns on or changes color) when the tip of the medical instrument is within a predefined depth range. For example, the depth of a target tumor may be predefined as a depth of interest during pre-operative planning, and the system may cause a visual indicator on the medical instrument to be activated when the tip of the medical instrument is at or close to this depth of interest.

In some examples, relative depth data may also be provided as output (e.g., visual, audio and/or haptic feedback) indicating whether or when the tip of the medical instrument is within a user-selected depth range. For example, after the surgeon has selected a depth range of interest (e.g., using a slider provided in a user interface), an audio output may be provided when the instrument tip is within the selected depth range.

The different output modalities may be provided in combination, and each output modality may be independently selected to output general or relative depth data. General and relative depth data may be provided simultaneously, for example by providing general depth data using one output modality while providing relative depth data using a different output modality. For example, a visual contour map of the surgical site may provide general depth data of the site at the same time that audio output provides relative depth data indicating the depth of the tip of the medical instrument relative to the surface of the site.

In some examples, different output devices may be used to simultaneously provide both general and relative depth data using the same output modality. For example, one visual display may display contour lines for the overall site of interest, while a second visual display may display relative depth data specific to the medical instrument.

Figure 12:
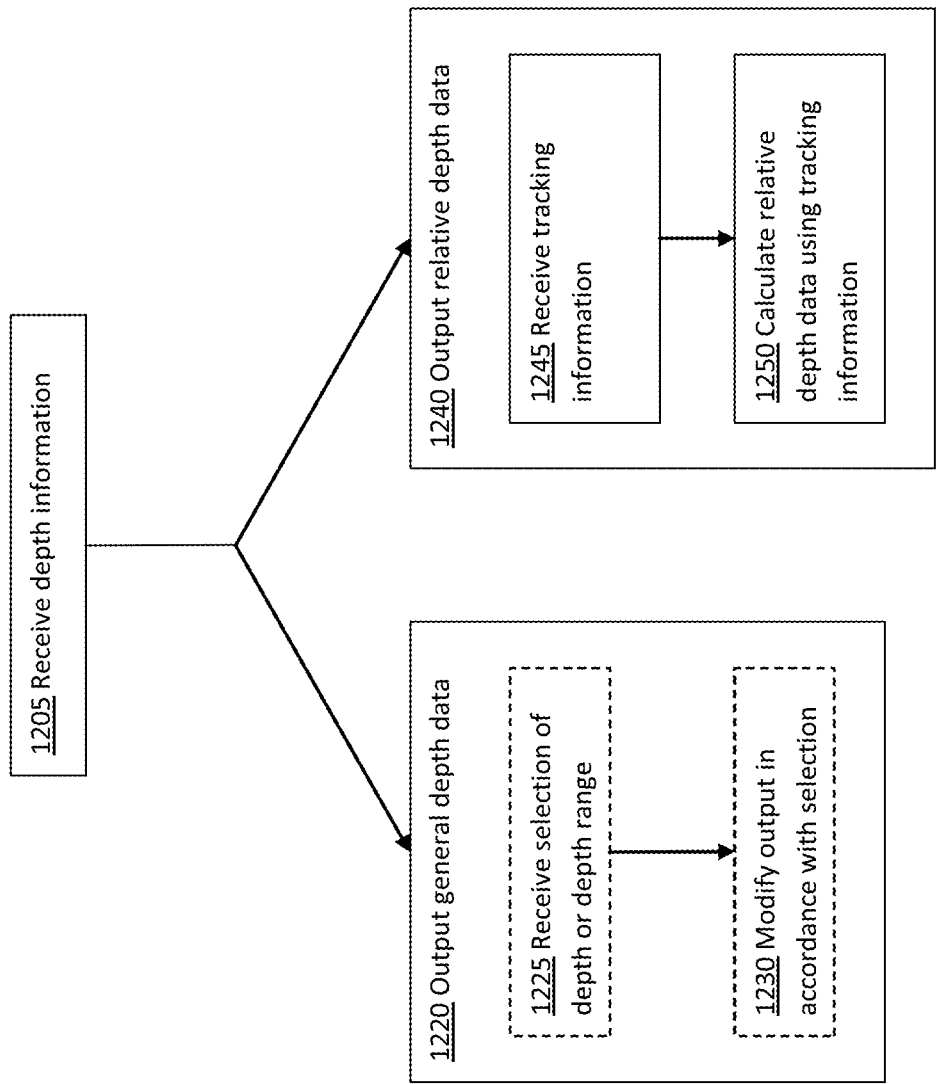
FIG. 12 is a flowchart illustrating an example method for providing depth information during a medical procedure.

FIG. 12 is a flowchart illustrating an example method for providing depth information. This example method may be performed by the control and processing system of the navigation system, for example.

At 1205, depth information is received. The depth information may include information about variations of depth over the site of interest. The depth information may be provided by any suitable depth detector, such as a 3D scanner (e.g., provided as a point cloud) or an imaging device (e.g., determined based on the DOF of the imaging device). The depth information may be repeatedly updated (e.g., automatically at set time intervals or in response to user input), in some examples. In some examples, it may be sufficient to obtain the depth information only once, since the site of interest may be sufficiently unchanging during the medical procedure.

The depth data may be outputted as general depth data, relative depth data, or both, and using different output modalities, as described above. For example, the user interface may provide selectable options to switch between different output modes and/or different output modalities.

For outputting general depth data, the method proceeds to 1220.

In some examples, the surgeon may select a certain depth or depth range at 1225.

At 1230, output of the general depth data may be modified in accordance with the selected depth or depth range. For example, a visual output may be selectively blurred, as described above.

For outputting relative depth data, the method proceeds to 1240.

At 1245, tracking information is received. The tracking information includes information about the position and/or orientation of the medical instrument. The tracking information may include information specific to the medical instrument tip. In some examples, the position and orientation of the medical instrument tip may be calculated from tracking of the medical instrument in general. The tracking information may be received from a tracking system of the navigation system that is tracking markers on the medical instrument, for example. Although shown as part of block 1240, the tracking information may be continuously received throughout the medical procedure, such as whenever the medical instrument is within an area of interest.

At 1250, the relative depth data is calculated using the tracking information. Calculation of the relative depth data includes relating the depth information of the site of interest to the position and/or orientation of the medical instrument, as described above. The relative depth data may then be outputted as appropriate.

In some examples, the blocks 1220 and/or 1240 may be performed for different selected output devices and modalities. The blocks 1220 and 1240 may both be performed.

Although the above discussion refers to the surgeon as being the user who controls and uses the examples of the present disclosure, it should be understood that the present disclosure is not limited to any specific user. In some examples, there may be a plurality of users involved.

While some embodiments or aspects of the present disclosure may be implemented in fully functioning computers and computer systems, other embodiments or aspects may be capable of being distributed as a computing product in a variety of forms and may be capable of being applied regardless of the particular type of machine or computer readable media used to actually effect the distribution.

At least some aspects disclosed may be embodied, at least in part, in software. That is, some disclosed techniques and methods may be carried out in a computer system or other data processing system in response to its processor, such as a microprocessor, executing sequences of instructions contained in a memory, such as ROM, volatile RAM, non-volatile memory, cache or a remote storage device.

A computer readable storage medium may be used to store software and data which when executed by a data processing system causes the system to perform various methods or techniques of the present disclosure. The executable software and data may be stored in various places including for example ROM, volatile RAM, non-volatile memory and/or cache. Portions of this software and/or data may be stored in any one of these storage devices.

Examples of computer-readable storage media may include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

Furthermore, at least some of the methods described herein may be capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

At least some of the elements of the systems described herein may be implemented by software, or a combination of software and hardware. Elements of the system that are implemented via software may be written in a high-level procedural language such as object oriented programming or a scripting language. Accordingly, the program code may be written in C, C++, J++, or any other suitable programming language and may comprise modules or classes, as is known to those skilled in object oriented programming. At least some of the elements of the system that are implemented via software may be written in assembly language, machine language or firmware as needed. In either case, the program code can be stored on storage media or on a computer readable medium that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner in order to perform at least one of the methods described herein.

While the teachings described herein are in conjunction with various embodiments for illustrative purposes, it is not intended that the teachings be limited to such embodiments. On the contrary, the teachings described and illustrated herein encompass various alternatives, modifications, and equivalents, without departing from the described embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

The invention claimed is:

1. A medical navigation system for use with a tracking system during a medical procedure on a patient, the tracking system configured to obtain tracking information about position and orientation of an instrument during the medical procedure, the medical navigation system comprising:

a depth detector configured to obtain depth information about variations in depth over a site of interest; and a controller in communication with the tracking system and the depth detector to receive the tracking information and the depth information, respectively, the controller having a processor coupled to a memory, the controller configured to enable selection of output representing relative depth data, general depth data, or both, and further configured to cause at least one output device to provide output representing relative depth data, general depth data, or both, in accordance with the selection, the at least one output device being a display device, and the controller further configured to cause the display device to display the output overlaid on an image of the site of interest, and to cause display of the output including changing a visual characteristic of contour lines overlaid on the image;

wherein the relative depth data is determined by the controller using the tracking information and the depth information, and represents the depth information relative to the position and orientation of the instrument; and wherein the general depth data represents the depth information over the site of interest independently of the position and orientation of the instrument;

wherein the image of the site of interest is a 3D rendering of a point cloud;

wherein the controller is further configured to cause display of the output including blurring at least one portion of the image corresponding to at least one portion of the site of interest outside of a predefined depth range relative to the distal end of the instrument.

2. The medical navigation system of claim 1, wherein the depth detector is separate from the tracking system.

3. The medical navigation system of claim 1, wherein the 3D rendering of the site of interest further comprises a 3D topographic map.

4. The medical navigation system of claim 1, wherein, when output of both relative depth data and general depth data is selected, the controller is configured to cause at least one output device to provide output representing the relative depth data, and to cause at least another one output device to provide output representing the general depth data.

5. The medical navigation system of claim 1 wherein the controller is further configured to cause display of the output including selective display of predefined colors in overlaid on the image, the predefined colors each being associated with a relative depth range.

6. The medical navigation system of claim 1 wherein changing the visual characteristic of the contour lines comprises one or more of changing a line style, a line thickness, a line color, and a line location.

7. The medical navigation system of claim 1 wherein the instrument has an operational axis, wherein the controller is further configured to:

calculate the depth information relative to a plane defined by the operational axis; and cause display of the output including displaying the visual characteristic of the contour lines to represent the depth information relative to a plane defined by the operational axis.

8. The medical navigation system of claim 1 wherein the controller is further configured to cause display of the output including visually highlighting at least one portion of the image corresponding to at least one portion of the site of interest within a predefined depth range relative to the distal end of the instrument.

9. The medical navigation system of claim 1, wherein the controller is further configured to cause the at least one output device to provide an audio output.

10. The medical navigation system of claim 9, wherein the audio output is representative of the relative depth data, comprises an audio pattern representing the general depth data, or is a combination thereof.

11. The medical navigation system of claim 1, wherein the controller is further configured to cause the at least one output device to provide a haptic output.

12. The medical navigation system of claim 11, wherein the haptic output is representative of the relative depth data, comprises a haptic pattern representing the general depth data, or is a combination thereof.

13. A method for use with tracking information about position and orientation of an instrument during a medical procedure on a patient, the method comprising:
receiving depth information about variations in depth over a site of interest;
enabling selection of output representing relative depth data, general depth data, or both;
providing output representing relative depth data, general depth data, or both, in accordance with the selection by displaying the output overlaid on an image of the site of interest; and
changing a visual characteristic of contour lines overlaid on the image; wherein
the relative depth data is determined using the tracking information and the depth information, and represents the depth information relative to the position and orientation of the instrument; and
wherein the general depth data represents the depth information over the site of interest independently of the position and orientation of the instrument;
wherein the image of the site of interest is a 3D rendering of a point cloud;
wherein the controller is further configured to cause display of the output including blurring at least one portion of the image corresponding to at least one portion of the site of interest outside of a predefined depth range relative to the distal end of the instrument.

14. The method of claim 13, wherein the depth information and the tracking information are obtained separately from each other.

15. The method of claim 13, wherein the 3D rendering further comprises 3D topographic map of the site of interest.

16. The method of claim 13, wherein the instrument has an operational axis, the method further comprising:
calculating the depth information relative to a plane defined by the operational axis; and
displaying the visual characteristic of the contour lines to represent the depth information relative to a plane defined by the operational axis.

17. The method of claim 13, wherein the output comprises at least one of a visual output, an audio output, a haptic output, and combinations thereof.

* * * * *